United States Patent [19]
Koljonen et al.

[11] Patent Number: 5,991,436
[45] Date of Patent: *Nov. 23, 1999

[54] APPARATUS AND METHOD FOR INSPECTING WIRE BONDS ON LEADS

[75] Inventors: Juha Tapio Koljonen, Needham; John Phillip Petry, III, West Newton, both of Mass.

[73] Assignee: Cognex Corporation, Natick, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 08/491,335

[22] Filed: Jun. 30, 1995

[51] Int. Cl.⁶ .................................................. G06K 9/00
[52] U.S. Cl. ......................................... 382/150; 382/203
[58] Field of Search .................................... 382/141, 146, 382/149, 150, 203, 209, 241; 348/86, 87, 90, 126; 356/237, 376, 392, 394, 397

[56] References Cited

U.S. PATENT DOCUMENTS

| | | | |
|---|---|---|---|
| 4,748,675 | 5/1988 | Suzuki et al. | 382/241 |
| 4,942,618 | 7/1990 | Sumi et al. | 382/154 |
| 5,015,097 | 5/1991 | Nomoto et al. | 382/150 |
| 5,030,008 | 7/1991 | Scott et al. | 356/394 |
| 5,145,099 | 9/1992 | Wood et al. | 228/9 |
| 5,245,671 | 9/1993 | Kobayashi et al. | 382/150 |
| 5,369,492 | 11/1994 | Sugawara | 348/126 |

FOREIGN PATENT DOCUMENTS 7-63528   3/1995   Japan .

OTHER PUBLICATIONS

"Automated Visual Inspection System for Bonded IC Wires *", Hiroyuki Tsukahara Masato Nakashima and TakehisaSugawara, Elsevier Science Publishers Ltd., Microelectronics Journal, 24 (1993) pp.625–633, No Month.

"Bonding Wire Microelectronic Interconnections", Bruce L. Gehman, IEEE Transactions on Components, Hybrids, and Manufacturing Technology, vol. CHMT–3, No.3, Sep. 1980, pp. 375–383.

"Wire Bonding–Towards 6–σ Yield and Fine Pitch", George G. Harman, IEEE Transactions on Components, Hybrids, and Manufacturing Technology, vol. 15, No. 6, Dec. 1992, pp. 1005–1012.

"Automated Vision System for Inspection of IC Pads and Bonds", Koduri K. Sreenivasan, Mandyam Srinath, and Alireza Khotanzad, IEEE Transactions on Components, Hybrids, and Manufacturing Technology, vol. 16, No. 3, May 1993, pp. 333–338.

*Primary Examiner*—Christopher S. Kelley
*Attorney, Agent, or Firm*—Russ Weinzimmer; Tracy Calabresi

[57] ABSTRACT

An apparatus and method are provided for automatic visual inspection of crescent-shaped wire bonds. The apparatus includes image acquisition means for acquiring an image of a wire and an image of a crescent-shaped wire bond. A search model is used that includes a crescent-modeling portion, and can also advantageously include a wire modeling portion. Search functionality is used to find an image of the crescent-shaped wire bond, using the search model, so as to provide location information regarding the location of the crescent base, and shape-match information regarding the reliability of the found location information. The invention is useful for verifying the correct position of the crescent bond to ensure good electrical contact. In addition, the invention greatly simplifies the task of two other important automated visual inspection steps: wire location and crescent shape determination. Presence/absence of the crescent bond can also be determined using this information.

34 Claims, 7 Drawing Sheets

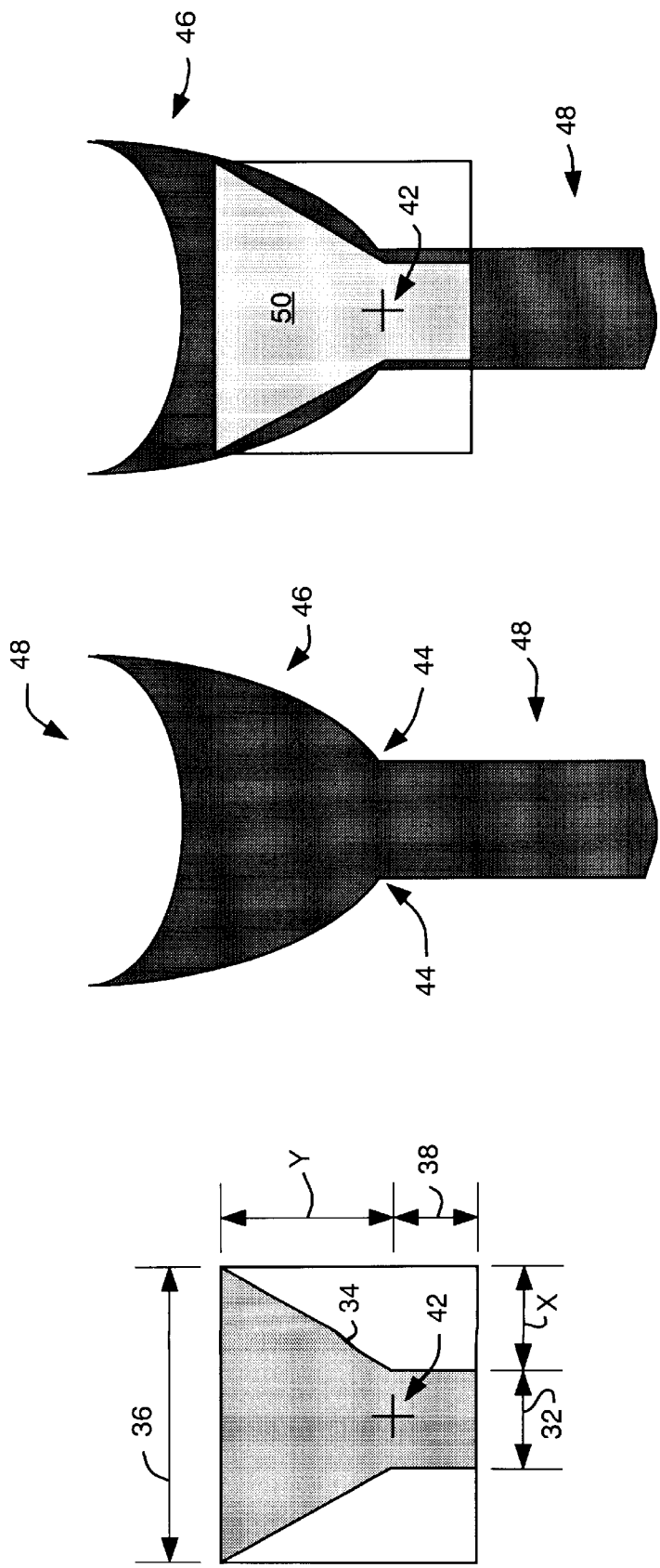

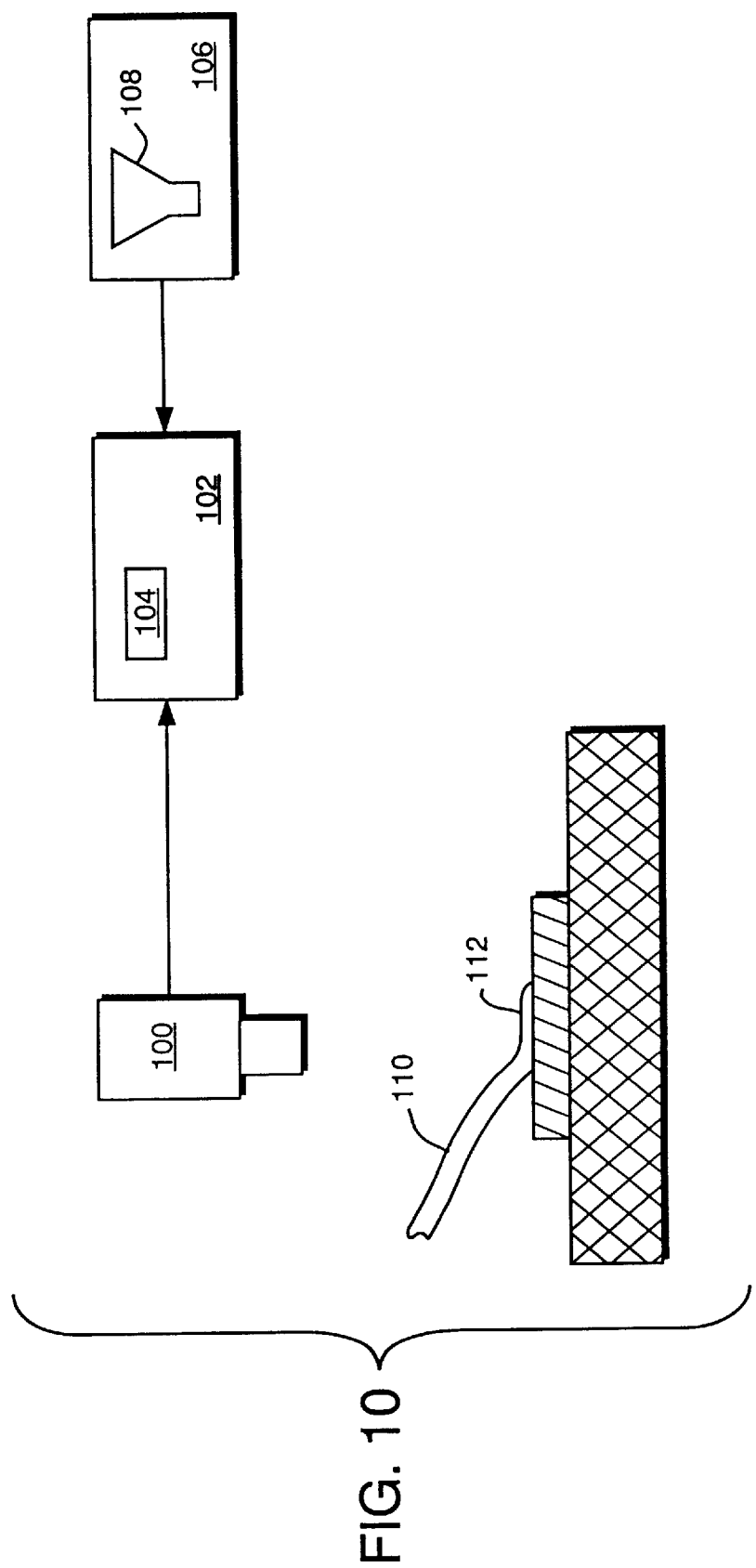

APPARATUS AND METHOD FOR INSPECTING WIREBONDS ON LEADS

FIELD OF THE INVENTION

This invention relates generally to machine vision, and particularly to automated visual inspection of wirebonds in semiconductor device packages.

BACKGROUND OF THE INVENTION

During the packaging of an integrated circuit device, it is necessary to connect the tiny electrical connection pads of the integrated circuit device (fabricated on a portion of a silicon wafer called a die) to the leads of a surrounding lead frame, the leads being more suited to electrical connection with other electronic devices.

Electrical connection of the pads on the die to the leads of the leadframe is accomplished by bonding a fine metal wire to each pad on the die to a corresponding lead on the surrounding lead frame. On each pad of the die, a "ball bond" is formed to bond the wire to the pad. On each corresponding lead of the lead frame, a "crescent bond", for example, is formed that bonds the wire to the lead. The formation of the crescent bond will now be described with reference to FIG. 1.

During bonding of the wire 10 to a lead 12, the wire 10 is fed through a capillary 14, i.e., a hollow metal tube, as the capillary 14 is moved from the ball bond (not shown) of the wire 10 on a pad (not shown) to the corresponding lead 12 of the lead frame (not shown). When it reaches a desired target position over the lead 12, the capillary 14 is pressed firmly against the lead 12, and can be heated and/or vibrated at high frequency. This causes the wire 10 to flatten, spread out, and metallurgically bond to the lead 12, thereby forming a crescent bond or crescent 16, the crescent including a portion that is bonded to the lead 12. The bond so-formed provides both an electrical and mechanical connection between the wire 10 and the lead 12. Both the shape and position of the crescent 16 with respect to the lead 12 indicate and affect the quality of the electrical and mechanical connection of the wire 10 to the lead 12. The pressing, vibrating, and/or heating of the capillary 14 on the lead 12 (using a "thermosonic" bonding process, for example) also causes the formation of a capillary indentation (not shown) on the lead 12, the image of which can be confused with the image of the crescent 16.

Referring to FIG. 2, a top view of a crescent bond is shown. The wire 10 extends until it widens and flattens to form the crescent 16. The bottom of crescent 16 is defined to be the crescent base 18. The position of the crescent base 18 is herein defined to be a point at the intersection of a longitudinal axis 20 that bisects the crescent 16 and a line 22 that can be drawn so as to demark the beginning of the transition from the wire 10 to the crescent 16. Also shown are the crescent tips 21 and the crescent edge 23.

Referring to FIG. 3, the characteristics of the crescent 16 depend on several factors, primarily the capillary diameter 24, the capillary wall thickness 26, and the capillary edge angle 28. The wire diameter, and the force, temperature, and frequency of the capillary vibration also contribute to determining the characteristics of the crescent 16.

During the manufacture of packaged integrated circuits, it is necessary to inspect the crescent bonds that are formed on the leads of the lead frame. Ideally this inspection is performed immediately after the bonding step, so that errors in size, shape, placement, or lack of presence of the crescent bond can be detected and corrected before or soon after the error is repeated.

Commonly, inspection of the crescent bond is performed off-line by a skilled operator that manually inspects only a statistically significant sample of bonds using an optical microscope at high magnification with shallow depth of focus so as to measure bond size, shape, and presence/absence of crescent bonds. Only a sample of the bonds are inspected because the part must be removed from the production line to be inspected.

As wirebond machines increase in throughput rate, and as the geometries of semiconductor devices shrink, automated visual inspection becomes increasingly critical for inspection, and as well as for process control. By automating the crescent bond inspection step, it becomes possible to detect defective bonds at the earliest possible moment in the production process. Thus, bad parts can be removed before they are used, or before other testing is done, thereby reducing rework costs. Also, wirebonder equipment can be adjusted to correct the error before other bad parts are created, thereby minimizing waste, improving quality, and improving yield.

In many machine vision applications, a template for use with normalized correlation search, for example, can be developed from an ensemble of good images, e.g., good images of good crescent bonds. However, this approach does not provide a robust solution, apparently due to the high degree of variation in crescent bond shape and image contrast found in industrial application settings. Templates trained in this way that are used for finding the location and shape of crescent bonds do not yield satisfactory performance.

SUMMARY OF THE INVENTION

An apparatus and method are provided for automatic visual inspection of crescent-shaped wire bonds. The apparatus includes image acquisition means, such as a video camera, for acquiring an image of a wire and an image of a crescent-shaped wire bond. A search model is used that includes a crescent-modeling portion. Search functionality is used to find an image of the crescent-shaped wire bond, using said search model, so as to provide at least one of location information regarding the location of the crescent base, and shape-match information regarding the reliability of the found location information.

In various preferred embodiments of the invention, the search model is a binary image, and the search model is a synthetic image. In other preferred embodiments of the invention, the search functionality includes template matching functionality, such as means for performing normalized correlation search.

In further preferred embodiments, the crescent-modeling portion of the search model includes at least a portion of a triangle, and the search model further includes a wire-modeling portion. Further, the wire-modeling portion can include at least a portion of a rectangle. In addition, the search model can be formed by overlapping a triangle and a rectangle.

In another preferred embodiment, the search model includes a narrow portion having a generally constant width along a longitudinal axis, and a wider portion having a width that increases along the longitudinal axis at about the same rate as a width of the crescent-shaped wire bond.

It is useful for the crescent-modeling portion to be generally smaller than the image of the crescent-shaped wire bond. Also, it is helpful for the wire-modeling portion to longitudinally extend approximately as far from the crescent base as the crescent-modeling portion longitudinally extends from the crescent base.

In other preferred embodiments, the crescent-modeling portion includes a trapezoid, and further, the trapezoid can usefully be symmetric about an axis that is perpendicular to its two parallel sides.

Also the wire modeling portion need not be connected to the crescent-modeling portion. In other embodiments, however, the wire modeling portion is continuous with the crescent-modeling portion. In an alternate embodiment, the wire-modeling portion is about the same width as the width of the wire.

Locating the position of the crescent base can be useful because it can be used to verify that the correct position of the crescent bond to ensure good electrical contact. Knowledge of the crescent base location also permits automatic position feedback to the wirebonding machine. In addition, locating the crescent base greatly simplifies the task of two other important automated visual inspection steps: wire location and crescent shape determination. Presence/absence of the crescent bond can also be determined using this information. Also, the position of the crescent is a good starting point for measuring its width, height, and/or center of mass.

BRIEF DESCRIPTION OF THE DRAWINGS

The invention will be more fully understood from the following detailed description, in conjunction with the accompanying figures, wherein:

FIG. 5 is a depiction of an exemplary synthetic binary template of the invention;

FIG. 6 is an image of a crescent bond, including a wire and a crescent base;

FIG. 7 is a depiction of the image of the crescent bond and its associated wire, with a image of the exemplary synthetic binary template of FIG. 5;

FIG. 10 is a schematic diagram of an exemplary embodiment of the invention.

DETAILED DESCRIPTION OF PREFERRED EMBODIMENTS OF THE INVENTION

Figure 1:
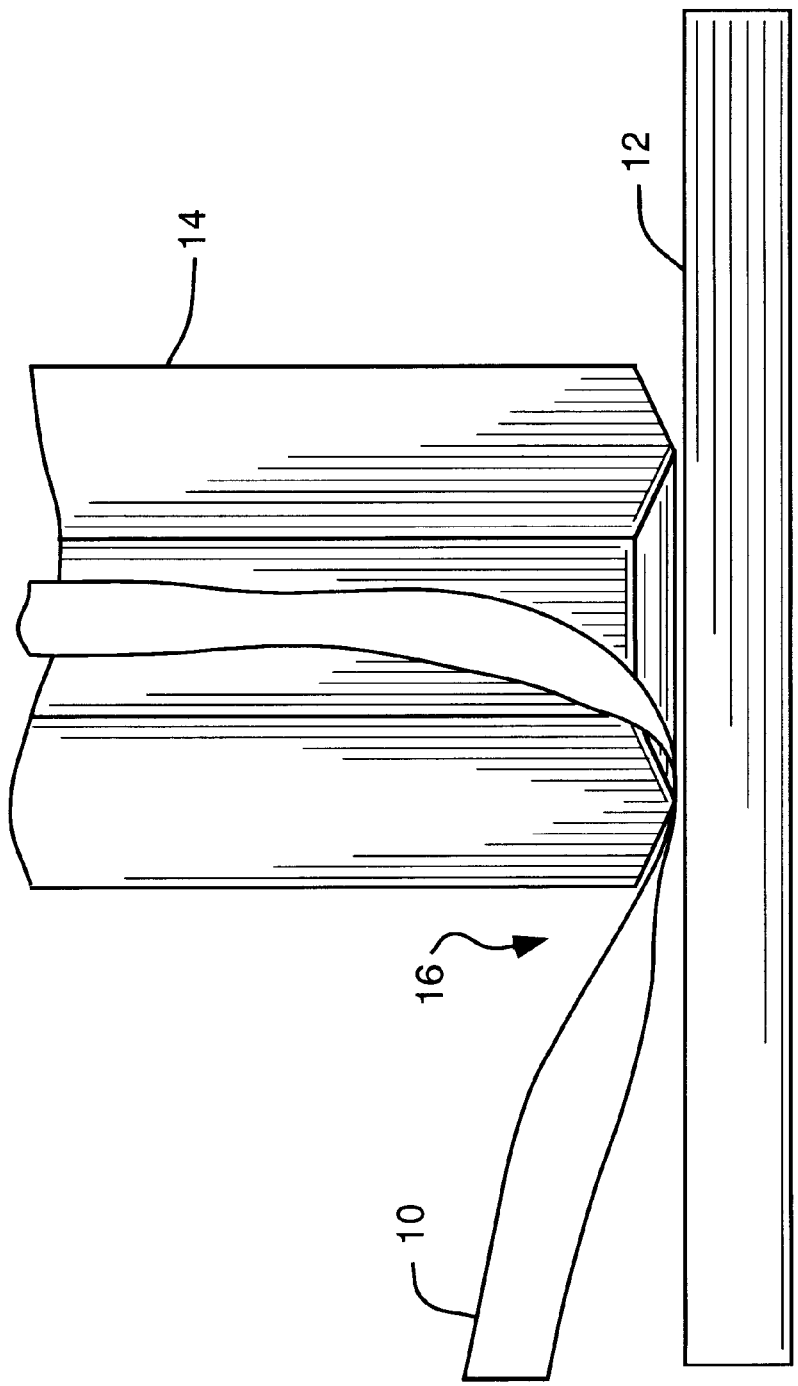
FIG. 1 is a side view of a capillary pressing a wire against a lead.
Figure 2:
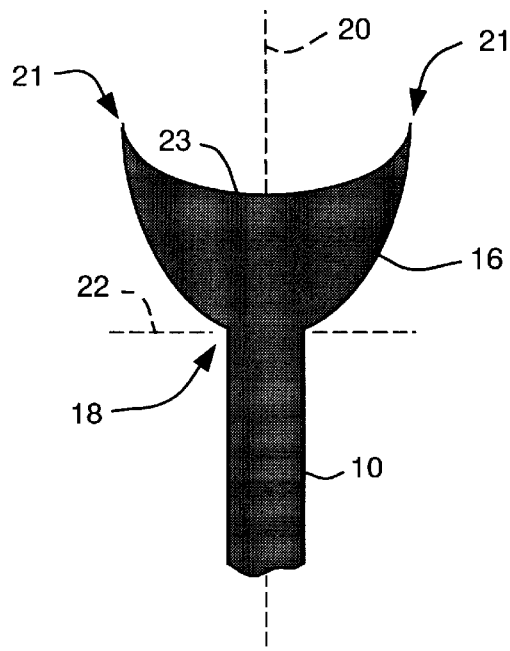
FIG. 2 is an top view of a wire and an associated crescent.
Figure 3:
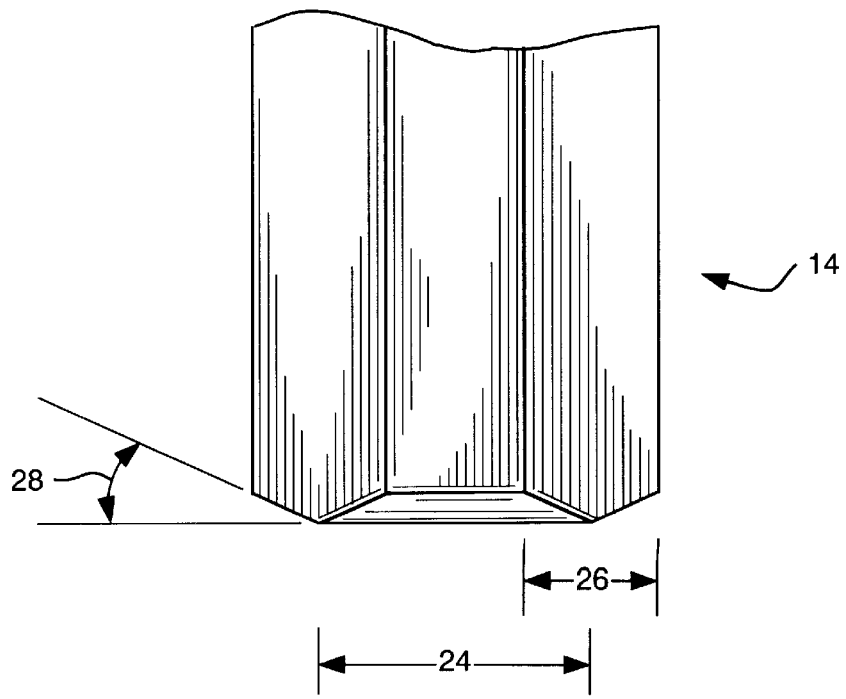
FIG. 3 is a cut-away side view of the capillary of FIG. 1.
Figure 4:
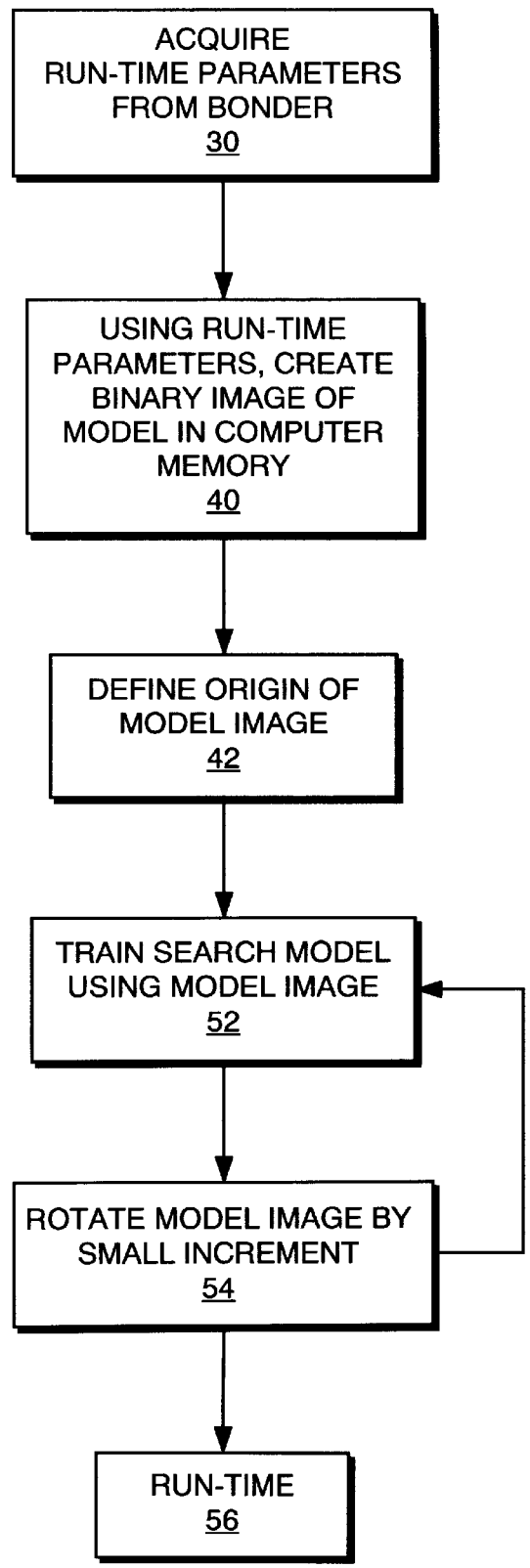
FIG. 4 is a flow chart of a preferred method for using a synthetic template of the invention.
Figure 8A:
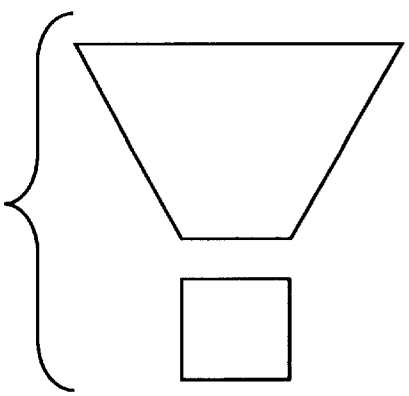
FIGS. 8A–8D are depictions of other synthetic binary model images of the invention.
Figure 8B:
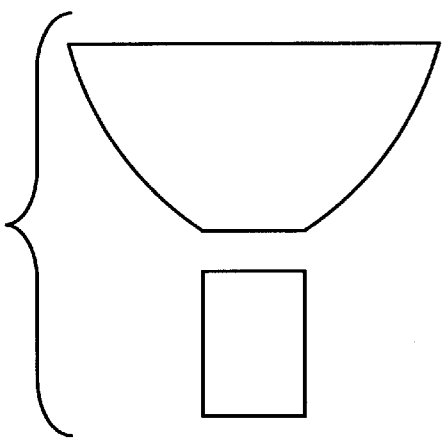
Figure 8C:
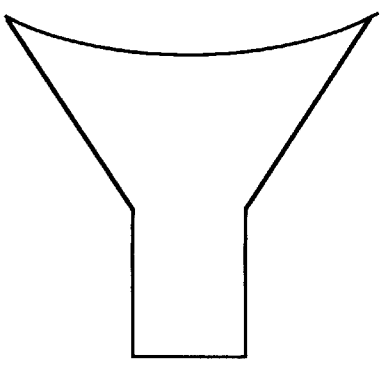
Figure 8D:
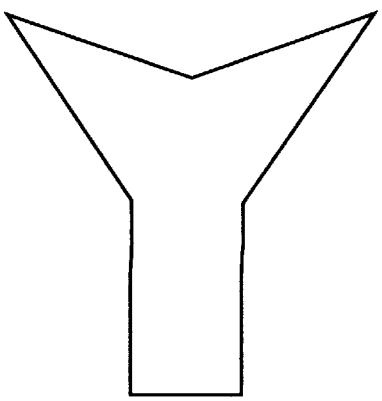

With reference to FIGS. 4 and 5, where reference number within parentheses denote method steps, at training time, run-time parameters, i.e., the wire diameter and the slope of the slope of the crescent, are acquired (30) from the bonder for defining the dimensions of the synthetic templates of the invention. The wire diameter 32 should be accurately measured. The slope (Y/X) of the crescent is fairly consistent for a given set of bonder parameters, such as capillary angle and bonder force.

Referring to FIG. 5, an exemplary synthetic binary template of the invention is shown, wherein the wire width 32 and the sloped line element 34 of slope (Y/X) have been used to create a binary image in computer memory (40). The template width 36 can be no wider than the corresponding portion of the widest crescent image (determined empirically or inferred from the size of the capillary), thereby determining X and Y, given the wire width 32 and the slope (Y/X). The template width 36 can be narrower than even the narrowest crescent image, so long as the template so-dimensioned is sufficiently insensitive to noise in the image to be searched. Likewise, the wire tail 38 must be long enough to be sufficiently robust to noise, but preferably, no longer.

Next, the origin of the model image must be defined (42). Referring to FIG. 6, preferably, the origin, indicated by the cross-hair 42, is defined to reside directly over the center of the image of the crescent base, i.e., between the intersection points 44 of the crescent portion 46 and the wire portion of an acquired image 48, when the image 48 is searched.

FIG. 7 shows a synthetic binary template 50 according to the invention, having an origin 42, wherein the template 50 was used to find the image of the crescent 46 and the wire 48, and is shown in the found position with respect to the crescent 46 and wire 48. Moreover, the origin 42 is shown to reside at the base of the crescent, i.e., the "crescent base".

FIGS. 8A, 8B, 8C, and 8D are examples of other synthetic binary model images that can provide comparable performance when used to find the crescent base of an acquired bond image. Note that the crescent portion of a model image according to the invention does not need to be continuous with the wire portion of the model image. Also note that each vertex of the crescent portion, and also of the wire portion does not need to be perfectly straight, but may deviate from straight in a curved and/or angled fashion without negating the usefulness of the model image according to the invention. An important constraint is that the model image should preferably be sized so as to fall substantially within the image of the crescent/wire image to be found by the search technique.

Also note that, according to the invention, the model image may also include pixels of varying grey value, and so may not be entirely binary. However, best results will be achieved when the model image is substantially binary, if not completely binary.

In addition, search techniques, such as normalized correlation search, as explained in *Computer Vision,* by Ballard and Brown, incorporated herein by reference, and as sold by Cognex Corporation, Natick Mass., return a parameter that indicates the quality of the found match. According to the invention, this parameter indicates the likelihood that the found image is the image of the sought crescent bond.

Note that a variety of search techniques can be employed according to the invention, such as edge based techniques, e.g., the Generalized Hough Transform, and area-based techniques other than normalized correlation, such as Sum of Absolute Differences, and Sign Correlation.

Referring again to FIG. 4, in accordance with the search methodology employed, such as normalized correlation search, sold by Cognex Corporation, a search model is trained (52) using the chosen model image, such one of the model images of FIG. 8. Next, the model image is rotated by a small angular extent (54), such as one degree, and steps (52) and (54) are repeated until the possible range of angular orientations of the acquired crescent images is spanned by variously rotated search models. When this is done, the acquired images may be searched at run-time.

Figure 9:
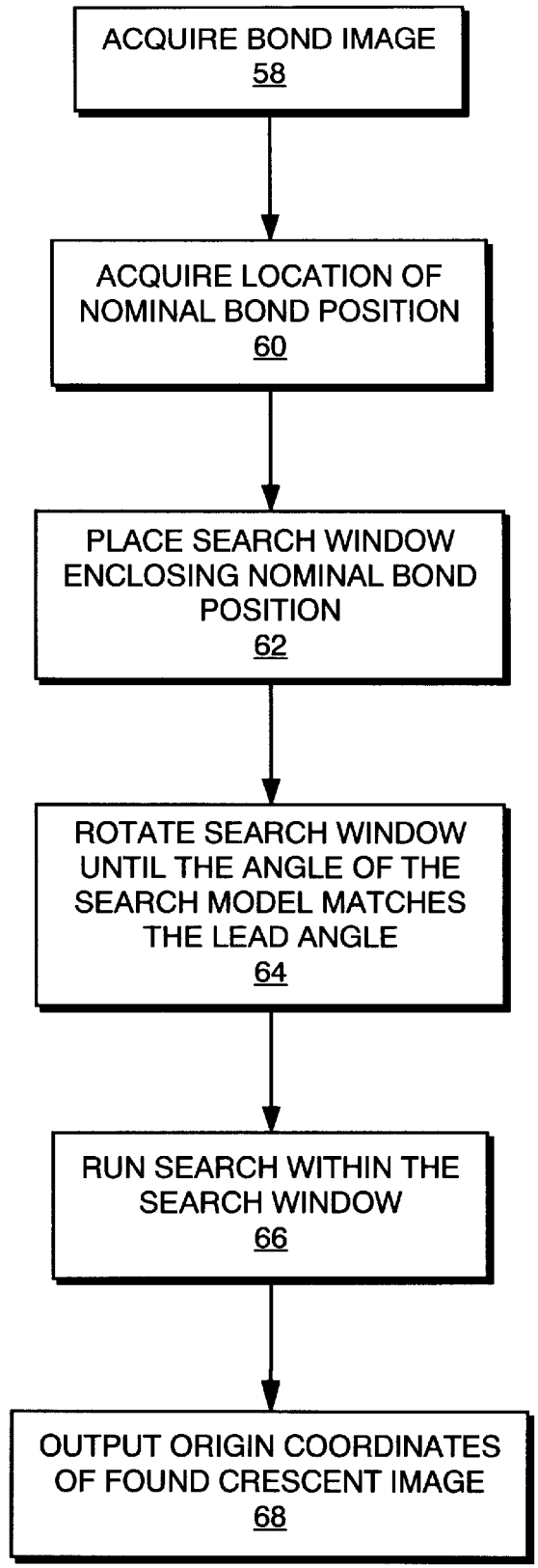
FIG. 9 is a flow chart of a run-time method for finding an image of a crescent bond in an image using the apparatus of the invention.

Referring to FIG. 9, at run-time, the actual crescent bonds, and their associated wires, are inspected. First, a digital image of a crescent bond is acquired (58), using a video camera, and associated video processor board, as is well understood by one skilled in the art of machine vision. Next, the location of the nominal search point, i.e., the nominal bond position, is acquired (60) from the wire bonder.

Next, a search window for establishing the limits of the search is placed so as to enclose the nominal bond position (62). Note that the actual location of the bond will differ from the nominal due to any physical displacement of the leads of the lead frame.

Next, the search window is rotated so that the lead angle aligns with the angle of the search model (64). Note that the bonder knows the lead angle, and can provide the lead angle to the vision system at run time.

Next, search is performed within the search window (66) using either a single model at a known angle, or using a number of models for a variety of angles, if the angle of the crescent bond is not known. The rotated model with the highest match score will be used for subsequent search operations.

Next, the position of the found image of the crescent bond is provided as the position of the crescent base within the search window, as indicated by the position of the coordinates of the origin of the model image (68). The coordinates of the actual position of the crescent base can be calculated by performing a reverse transform from the rotated image coordinates to the un-rotated image coordinates, and then to the physical coordinates represented by the pixels of the un-rotated image of the crescent bond. The pixel to physical coordinate transformation is performed by the wirebonder. FIG. 10 generally shows image acquisition means 100, such as a video camera, and a processor 102 connected thereto, which processor 102 includes a search means 104, preferably implemented as software executable on the processor 102. Preferred search means include "normalized correlation search", such as sold by Cognex Corporation, Natick Mass. Normalized correlation search is well-known in the art. The processor 102 is also connected to a memory device 106, such as a RAM chip or a floppy disk, for storing data that represents a search model 108, examples of such search models being shown in FIGS. 5, 6, 7, and 8A–8D. The image acquisition means 100 acquires an image of a wire 110 and a crescent-shaped bond 112.

Uses of the Position of the Crescent Base

Locating the position of the crescent base is useful because it can be used to verify that the crescent bond does not lie too close to the edge of a lead to ensure good electrical contact. Knowledge of the crescent base location also permits automatic feedback to the wirebonding machine to compensate for positional inaccuracies or drift. In addition, locating the crescent base greatly simplifies the task of two other important automated visual inspection steps: wire location and crescent shape determination. If the bond is poorly formed, the wire will sometimes break near the crescent. Knowing where the wire joins the crescent makes it possible to verify that the wire is connected thereto. Also, the position of the crescent is a good starting point for measuring its width, height, and/or center of mass, parameters that are useful for determining whether the crescent bond is well-formed and well-positioned.

The match score returned by the search functionality can be compared to a threshold that can be set so that match scores that do not meet or exceed the threshold indicate the high likelihood of the absence of the crescent bond, resulting in a rejection of the bond. To achieve further certainty that a crescent bond is not present, an attempt to locate an associated wire can be made. The absence of the wire strongly confirms the absence of a crescent bond. It is also possible to observe the presence of a crescent bond while the absence of an associated wire is also observed. In this case, such a bond would also be rejected.

Other modifications and implementations will occur to those skilled in the art without departing from the spirit and the scope of the invention as claimed. Accordingly, the above description is not intended to limit the invention except as indicated in the following claims.

What is claimed is:

1. An apparatus for automatic visual inspection of a crescent-shaped wire bond, said crescent-shaped wire bond including a crescent base, the apparatus comprising:

image acquisition means for acquiring an image of a wire and an image of a crescent-shaped wire bond;

a search model having a crescent-modeling portion that is of a shape that is different from said image of said crescent-shaped wire bond and includes at least a portion of a triangle; and search means for searching for said image of said crescent-shaped wire bond, using said search model, so as to provide at least one of location information regarding the location of said crescent base, and shape-match information regarding the shape of said crescent-shaped wire bond.

2. The apparatus of claim 1, wherein said search model is a binary image.

3. The apparatus of claim 1, wherein said search model is a synthetic image.

4. The apparatus of claim 1, wherein said search means includes means for template matching.

5. The apparatus of claim 4, wherein said means for template matching includes means for performing normalized correlation search.

6. The apparatus of claim 1, wherein said search model further includes a wire-modeling portion that is a shape that is different from said image of said wire.

7. The apparatus of claim 6, wherein said wire-modeling portion includes at least a portion of a rectangle.

8. The apparatus of claim 1, wherein said search model is formed by overlapping the at least a portion of a triangle and a rectangle.

9. The apparatus of claim 1, wherein said search model includes a narrow portion having a generally constant width along a longitudinal axis, and a wider portion at an opposed end having a width that increases along said longitudinal axis at about the same rate as a width of said crescent-shaped wire bond.

10. The apparatus of claim 1, wherein said crescent-modeling portion is generally smaller than said image of said crescent-shaped wire bond.

11. The apparatus of claim 10, wherein said wire-modeling portion longitudinally extends approximately as far from said crescent base as said crescent-modeling portion longitudinally extends from said crescent base.

12. The apparatus of claim 1, wherein said portion of a triangle of the said crescent-modeling portion is a trapezoid.

13. The apparatus of claim 12, wherein said trapezoid is symmetric about an axis that is perpendicular to its two parallel sides.

14. The apparatus of claim 6, wherein said wire modeling portion is not connected to said crescent-modeling portion.

15. The apparatus of claim 6, wherein said wire modeling portion is continuous with said crescent-modeling portion.

16. The apparatus of claim 6, wherein said wire-modeling portion is about the same width as the width of said wire.

17. A method for automatic visual inspection of a crescent-shaped wire bond, said crescent-shaped wire bond including a crescent base, comprising:

acquiring an image of a wire and an image of a crescent-shaped wire bond;

providing a search model having a crescent modeling portion that is of a shape that is different from said image of said crescent-shaped wire bond and includes at least a portion of a triangle; and searching for said image of said crescent-shaped wire bond, using said search model, so as to provide at least one of location information regarding the location of said crescent base, and shape-match information regarding the shape of said crescent-shaped wire bond.

18. The method of claim 17, wherein said search model is a binary image.

19. The method of claim 17, wherein said search model is a synthetic image.

20. The method of claim 17, wherein searching includes template matching.

21. The method of claim 17, wherein template matching includes performing normalized correlation search.

22. The method of claim 17, wherein said search model further includes a wire-modeling portion that includes at least a portion of a polygonal approximation of said image of said wire.

23. The method of claim 22, wherein said wire-modeling portion includes at least a portion of a rectangle.

24. The method of claim 17, wherein said search model is formed by overlapping the at least a portion of a triangle and a rectangle.

25. The method of claim 17, wherein said search model includes a narrow portion having a generally constant width along a longitudinal axis, and a wider portion at an opposed end having a width that increases along said longitudinal axis at about the same rate as a width of said crescent-shaped wire bond.

26. The method of claim 17, wherein said crescent-modeling portion is generally smaller than said image of said crescent-shaped wire bond.

27. The method of claim 26, wherein said wire-modeling portion longitudinally extends approximately as far from said crescent base as said crescent-modeling portion longitudinally extends from said crescent base.

28. The method of claim 17, wherein said portion of a triangle of the said crescent-modeling portion is a trapezoid.

29. The method of claim 28, wherein said trapezoid is symmetric about an axis that is perpendicular to its two parallel sides.

30. The method of claim 22, wherein said wire-modeling portion is not connected to said crescent-modeling portion.

31. The method of claim 22, wherein said wire-modeling portion is continuous with said crescent-modeling portion.

32. The method of claim 22, wherein said wire-modeling portion is about the same width as the width of said wire.

33. The apparatus of claim 1, wherein said crescent-modeling portion of said search model includes at least a portion of a polygonal approximation of said image of said crescent-shaped wire bond.

34. The method of claim 17, wherein said crescent-modeling portion of said search model includes at least a portion of a polygonal approximation of said image of said crescent-shaped wire bond.

\* \* \* \* \*